(12) United States Patent
Coroneo (10) Patent No.: US 9,050,310 B2
(45) Date of Patent: Jun. 9, 2015

(54) TREATMENT OF OCULAR LESIONS

(76) Inventor: Minas Theodore Coroneo, Randwick (AU)

(*) Notice: Subject to any disclaimer, the term of this patent is extended or adjusted under 35 U.S.C. 154(b) by 1729 days.

(21) Appl. No.: 11/159,153

(22) Filed: Jun. 23, 2005

(65) Prior Publication Data

US 2005/0287115 A1    Dec. 29, 2005

Related U.S. Application Data

(60) Provisional application No. 60/651,457, filed on Jun. 25, 2004.

(51) Int. Cl.
    *A61K 38/21*      (2006.01)
    *C07K 14/56*      (2006.01)
    *A61K 31/07*      (2006.01)
    *A61K 31/203*     (2006.01)

(52) U.S. Cl.
    CPC .............. *A61K 31/203* (2013.01); *C07K 14/56* (2013.01); *A61K 31/07* (2013.01); *A61K 38/212* (2013.01)

(58) Field of Classification Search
    None
    See application file for complete search history.

(56) References Cited

U.S. PATENT DOCUMENTS

| | | |
|---|---|---|
| 4,193,931 A | 3/1980 | Loeliger |
| 4,539,134 A | 9/1985 | Martin et al. |
| 4,801,733 A | 1/1989 | Wuest et al. |
| 4,831,052 A | 5/1989 | Shudo |
| 4,833,240 A | 5/1989 | Maignan et al. |
| 4,874,747 A | 10/1989 | Shroot et al. |
| 4,879,284 A | 11/1989 | Lang et al. |
| 4,898,864 A | 2/1990 | Maignan et al. |
| 4,925,979 A | 5/1990 | Shudo |
| RE33,533 E | 2/1991 | Shroot et al. |
| 5,004,730 A | 4/1991 | Philippe et al. |
| 5,124,473 A | 6/1992 | Shroot et al. |
| 5,198,567 A | 3/1993 | Lang et al. |
| 5,391,569 A | 2/1995 | Brion et al. |
| 5,693,493 A | 12/1997 | Robinson et al. |
| 5,968,493 A | 10/1999 | Dornoff |
| 6,030,964 A | 2/2000 | Hibi et al. |
| 6,133,309 A | 10/2000 | Bollag et al. |
| 6,147,244 A | 11/2000 | McKenna et al. |
| 6,593,493 B1 | 7/2003 | Ardecky et al. |
| 2002/0001615 A1 | 1/2002 | Nanus |

FOREIGN PATENT DOCUMENTS

| | | |
|---|---|---|
| EP | 0718285 | 6/1996 |
| WO | WO 93/21146 | 10/1993 |
| WO | WO 94/12880 | 6/1994 |
| WO | WO 94/15901 | 7/1994 |
| WO | WO 94/15902 | 7/1994 |
| WO | WO 94/17796 | 8/1994 |
| WO | WO 94/20093 | 9/1994 |
| WO | WO 96/05165 | 2/1996 |

OTHER PUBLICATIONS

Coroneo M.T. et al. The pathogenesis of pterygiua. Current Opinion in Ophthalmology. 1999, vol. 10, p. 282-288.*
Lingen M.W. et al. Retinoic acid and interferon-alpha act synergistically as antiangiogenic and antitumor agents against human head and neck squamous cell carcinoma. Cancer Research, 1998, vol. 58, p. 5551-5558.*
Schechter B.A., et al. Regression of presumed primary conjuncitaval and corneal intraepithelial neoplasia with topical interferon alpha-2b. Cornea, 2002, vol. 21(1), p. 6-11.*
Herbort C.P. et al. Topical retinoic acid in dysplastic and metaplastic keratinization of corneoconjuncitval epithelium. Graefe's Arch. Clin. Exp. Ophthalmol., 1988, vol. 226, p. 22-26.*
Moore, D.M. et al. Retinoic acid and interferon in human cancer: Mechanistic and clinical studies. Seminars in Hematology, 1994, vol. 31(4), p. 31-37.*
Goldstein D, et al. The role of interferon in cancer therapy: A current perspective. CA Cancer J. Clin., 1988, vol. 38, vol. 258-277.*
Amano et al, *Br. J. Ophthalmol.*, 84:618-621 (2000).
Rubinfeld et al, *Ophthalmology*, 99(11):1647-1654 (1992).
MacKenzie et al, *Ophthalmology*, 98(12):1776-1781 (1991).
Chen et al, *Am J. of Ophthalmology*, 120:151-160 (1995).
Erie et al, *Ophthalmology*, 93(2):176-183 (1986).
Heigel et al, *Brief Reports*, 124(3):397-399 (1997).
Tabin et al, *Ophthalmology*, 104(3):485-492 (1997).
Wright, *Trans. Ophthalmol.*, 104:869-874 (1985).
Maskin et al, *Arch. Ophthalmol.*, 112:1145-1146 (1994).
Peck et al, "The Retinoids: Biology, Chemistry and Medicine", pp. 631-658, Raven Press, New York (1994).
Simoni et al, *Pure Appl. Chem.*, 73(9):1437-1444 (2001).
Kagechika et al, *J. Med. Chem.*, 32:834-840 (1989).
Kagechika et al, *J. Med. Chem.*, 32:1098-1108 (1989).
Kagechika et al, *J. Med. Chem.*, 32:2292-2296 (1989).
Boehm et al, *J. Med. Chem.*, 37:2930-2941 (1994).
Boehm et al, *J. Med. Chem.*, 38:3146-3155 (1995).
Allegretto et al, *J. of Biol. Chem.*, 270(41):23906-23909 (1995).

(Continued)

*Primary Examiner* — Robert Landsman
*Assistant Examiner* — Bruce D Hissong
(74) *Attorney, Agent, or Firm* — Sughrue Mion, PLLC (57) ABSTRACT

Methods for the treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface are described. Also described are uses and eyedrop formulations for the treatment of eye surface lesions.

31 Claims, 7 Drawing Sheets

(56) References Cited

OTHER PUBLICATIONS

Bissonnette et al, *Molecular and Cellular Biology*, 15(10):5576-5585 (1995).
Beard et al, *J. Med. Chem.*, 38:2820-2829 (1995).
Dawson et al, *J. Med. Chem.*, 32:1504-1517 (1989).
Di Girolamo et al, *Progress in Retinal and Eye Research*, 23:195-228 (2004).
Di Girolamo et al, *Investigative Ophthalmomogy & Visual Science*, 41(3):671-679 (2000).
Di Girolamo et al, *Investigative Ophthalmomogy & Visual Science*, 41(11):3430-3437 (2002).
Nolan et al, *American J. of Pathology*, 162(2):567-574 (2003).
Di Girolamo et al, *Investigative Ophthalmomogy & Visual Science*, 44(11):4705-4714 (2003).
Di Girolamo et al, *Investigative Ophthalmomogy & Visual Science*, 167(2):489-497 (2005).
Robert J. Motzer et al., "Interferon Alfa-2a and 13-*cis*-Retinoic Acid in renal Cell Carcinoma: Antitumor Activity in a Phase II Trial and Interactions In Vitro", Journal of Clinical Oncology, 1995, 13(8):1950-1957.
Walter M. Stadler et al., "Multicenter Phase II Trial of Interleukin-2, Interferon-α, and 13-*cis*-Retinoic Acid in Patients with Metastatic Renal-Cell Carcinoma", Journal of Clinical Oncology, 1998, 16(5):1820-1825.
Angelo Rosolen et al., "Effects of all-trans retinoic acid and interferon α in peripheral neuroectodermal tumor cell cultures and xenografts", International Journal of Oncology, 1998, 13:943-949.

* cited by examiner

TREATMENT OF OCULAR LESIONS

CROSS-REFERENCE TO RELATED APPLICATION

This application claims benefit of Provisional Application No. 60/651,457, filed Jun. 24, 2004. The entire disclosure of which is incorporated herein by reference.

TECHNICAL FIELD

The present invention relates to the treatment of ocular lesions. Particularly, the invention relates to compositions, uses and non-surgical therapeutic treatments for ocular lesions with a combination of interferon alpha ($\alpha$) and retinoids.

BACKGROUND OF THE INVENTION

Pterygium is an invasive and proliferative disease of the human ocular surface particularly prevalent in sun-exposed individuals. Histological examinations have identified foci of connective tissue elastosis and regions of severely damaged Bowman's membrane, suggesting either direct damage due to solar radiation or indirect damage due to excessive proteolytic activity. Pterygia are characterised by an inflammatory infiltrate, composed of neutrophils, mast cells, and lymphocytes, and can present with a prominent vascular reaction likely to be exacerbated by excessive cytokine and growth factor production by resident cells as well as infiltrating inflammatory cells.

Pterygium appears as a wedge-shaped fibrovascular growth of conjunctiva (the white of the eye) that extends onto the cornea. Whilst benign lesions, pterygia may become inflamed, may create instability of the pre-corneal tear film creating a symptomatic dry eye, may induce irregular cornea warpage and/or may obscure the visual axis. The standard therapeutic treatment for such pterygia involves surgical removal.

Surgical removal of pterygia involves ocular anaesthesia, patient sedation, and operative surgical pterygium removal where the pterygium is dissected away from ocular tissue. Pterygia have the propensity to regrow following their surgical removal. In an attempt to prevent regrowth of the pterygium, an ocular surgeon may remove some of the surface tissue of affected eye and suture it into the bead of the excised pterygium. Alternatively, an anti-metabolite such as mitomyacin C may be applied to the site of pterygium removal. Amano et al (*B. R. J. Ophthalmol.*, 2000: 84, 618-621) described pterygium recurrence in patients who underwent pterygium surgery with associated mitomyacin C or $\beta$-irradiation treatment to reduce pterygium regrowth. In a retrospective study of 164 patients pterygium regrowth following mitomyacin C or $\beta$-irradiation treatment was respectively 8.74% and 23%. Topical antipoliferatives used in the eye for the treatment of lesions, such as to prevent pterygium regrowth, are ocularly corrosive. Complications of topical ocular mitomyacin C include corneoscleral melting, cataract and secondary glaucoma (Rubinfeld et al, *Ophthalmology*, 1992, 99: 1647-1654). $\beta$-irradiation to reduce pterygium regrowth has been associated with scleral necrosis and secondary infections (MacKenzie et al, *Ophthalmology*, 1991: 98, 1776-1781).

Recurrent pterygium following surgery are often more aggressive than the original pterygium showing aggressive fibrovascular growth (Chen et al, *Am. J. Ophthalmol.* 1995: 120, 151-160).

Thus, notwithstanding surgical removal of pterygium, with its attendant costs and risk of complications, pterygium regrow. The treatments to prevent pterygium are associated with side effects, and do not prevent pterygium regrowth in many cases.

Pinguecula is a benign, yellowish brown proliferative growth that forms on the conjunctiva. Pinguecula may cause irritation and scratchiness of the eye, dry eye, inflammation of the conjunctiva and effect appearance of the eye. Inflamed pinguecula, which cause ocular irritation or become unsightly, may require surgical removal. However, the post-operation scar may be as cosmetically objectionable as the pinguecula and pinguecula regrowth may occur following surgical removal.

Ocular surface dysplasias of the eye, such as limbal epithelial dysplasia, are proliferative diseases which form lesions in the form of cellular masses on the surface of the eye. These lesions may cause eye irritation, obscure vision, disrupt the tear film and/or be cosmetically unsightly. Standard treatments of such dysplasias comprise surgical excision and/or topical mitomyacin C treatment. Problems of lesion recurrence and the corrosive nature of anti-proliferative agents, such as mitomyacin C, remain a problem for the treatment of ocular surface dysplasias.

Ocular neoplastic disorders, such as malignancies of the limbus and eyelids in humans and animals may cause ocular irritation, visual disturbance, disturbance of the tear film (with associated dry eye) and eye pain, particularly as the neoplastic lesion increases in size. Ocular neoplasms may lead to potentially fatal invasive carcinoma or eye loss. The standard treatment for ocular neoplastic disorders, such as squamous cell carcinoma of the limbus, intraepithelial neoplasia of the cornea and conjunctiva, involve surgical removal of the malignant lesion and adjunctive therapy including cryotherapy, radiotherapy, immunotherapy and topical cytostatic agents. Recurrence rates following surgical excision may be as high as 54% (Erie et al, "Conjunctival and corneal intraepithelial and invasive neoplasia", *Ophthalmology* 1986, 93: 176-183). Topical cysostatic agents such as mitomyacin C and 5-fluorouracil may impair physiological corneal epithelial replacement (Heigle et al, "Treatment of recurrent conjunctival epithelial neoplasia with topical mitomyacin C" *Am. J. Ophthalmol.* 1997: 124, 397-399). Surgical treatments, together with use of cytostatic agents, cryotherapy or radiation remain unsatisfactory (Tabin et al, *Ophthalmology* 1996: 104, 485-492; Lee, A., Hirst, L., *Survey of Ophthalmology*, 1995: 39, No. 6, 429-450).

Neutrophic keratitis, fibrosis of conjunctive drainage blebs in glaucoma and viral disorders of the eye have no particularly satisfactory treatment.

Interferon a has been proposed for the treatment of limbal dysplasia (Maskin, S. L., *Arch. Ophthalmol.* 1994, 1112-1114-1146) and ocular squamous cell carcinoma. Similarly, retinoic acid has been proposed for the treatment of dysplasia of the corneal epithelium (Wright, P. *Trans. Opthalmol. Soc. UK* 1985, 104: 869-74). However, such treatments have low efficacy in preventing lesion resolution and/or lesion recurrence compared with surgical treatments and have not been developed for patient treatment.

SUMMARY OF THE INVENTION

Unexpectedly, it has been found by the present inventor that the combination of interferon a and retinoid is effective in the treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface.

The combined treatment of the aforementioned ocular disorders with interferon α and retinoid may avoid the need for surgery for lesion removal and is effective in preventing lesion recurrence.

In accordance with a first aspect of the present invention there is provided a method for the treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface, which comprises administering to the surface of the eye of a subject in need of such treatment a therapeutically effective amount of interferon α and retinoid.

In accordance with a second aspect of the present invention there is provided an eyedrop formulation of interferon α and retinoid for the combination treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface.

In accordance with a third aspect of the present invention there is provided use of interferon α and retinoid in the manufacture of eyedrop medicaments for the treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface.

DETAILED DESCRIPTION

As used herein, the term "retinoid" refers to a natural or synthetic vitamin A analogue or other compound is an agonist of one or both nuclear retinoic acid receptor (RAR) and retinoic X receptor (RXR) each of which is encoded by three separate genes designated α, β, and γ (Peck, G. L., and Di Giovanni, J. J. "The retinoids: biology, chemistry and medicine", pp 631-658, Raven Press, New York, (1994)) the contents of which are incorporated herein by reference.

Preferred retinoids include retinoic acid, all-trans retinoic acid, 9-cis-retinoic acid and It has surprisingly been found by the present inventor that the combination of interferon α and retinoid is effective in the treatment of ocular lesions, particularly lesions of the surface of the eye, selected from ocular lesions, particularly diseases of the surface of the eye selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface.

The present invention in its various aspects includes the non-surgical treatment of the aforementioned conditions, in particular amelioration of the condition without recurrence, in contrast to the prior art.

In accordance with a first aspect of the present invention there is provided a method for the treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface, which comprises administering to the surface of the eye of a subject in need of such treatment a therapeutically effective amount of interferon α and retinoid.

The interferon α and retinoid may be administered by instilling eyedrops into the eye over a treatment period until the particular condition being treated resolves. The interferon α and retinoid may be administered sequentially or concurrently. Preferably, the interferon α is administered one or more times daily, and the retinoid is administered sequentially on every second day during treatment. The time interval between interferon α administration and retinoid administration in an embodiment of this invention is up to about 36 hours, such as 24 to 36 hours.

The interferon α is preferably interferon α, more preferably α-2b. The interferon α may be instilled into the eye in an amount from about $1 \times 10^4$ to about $1 \times 10^6$ international units (IU) per day, more preferably $1 \times 10^5$ to $1 \times 10^6$ IU per day, still more preferably $1 \times 10^6$ IU per day.

Retinoid may be administered to the eye in an eyedrop composition. Retinoid may be instilled into the eye in an amount of from about 0.05 μg to about 50 μg every second day, for example 1-20 μg, 5-15 μg or 5-10 μg. Retinoid eye drops may contain, for example a dosage of 0.005 to 0.15% retinoid in an ocularly compatible vehicle. A particularly preferred dosage form is from 1 to 2 drops every second day of an 0.01% w/w retinoid eye drop composition.

Eyedrop vehicles comprise ocularly acceptable carriers and excipients. Examples of pharmaceutically acceptable carriers and excipients include one or more of boric acid, sodium sulphate, sodium chloride, tyloxapol, preservatives such as benzylconium chloride, glycerol, and sterile water.

Where interferon α and retinoid are administered concurrently, they may be included nt he same eyedrop composition for instillation into the eye.

Prior to the treatment of ocular lesions in humans or animals by instillation into the eye of a combination of interferon α and retinoid, or during such treatment, interferon α may be administered by intralesion injection particularly during an initial treatment period, in an amount from 0.5 to 5 million international units, preferably from 1 to 3 million international units administered interlesionally for seven to 14 days. For example, interlesional interferon α may be administered twice weekly over a two week period from one to three times per week, preferably twice per week over a two week period.

The retinoid is an agonist of one or both of the retinoic acid recepor (RAR) and retinoid X receptor (RXR). Standard in vitro tests for receptor binding may be carried out to determine binding to RAR and RXR, for example as described in De Simoni et al, *Pure Appln. Chem. Vol* 73, No. 9, pp 1437-1444, 2001. RAR and RXR retinoid agonists, including both RAR specific and RXR specific agonists have been previously identified. See for example, WO 94/15902, WO 93/21146, WO 94/15901, WO 94/12880, WO 94/17796, WO 94/20093, WO 96/05165 and International Application No. PCT/US93/10166; European Patent Applications Nos. 87110303.2, 87309681.2 and EP 0718285; U.S. Pat. Nos. 4,193,931, 4,539,134, 4,801,733, 4,831,052, 4,833,240, 4,874,747, 4,879,284, 4,898,864, 4,925,979, 5,004,730, 5,124,473, 5,198,567, 5,391,569, Re 33,533, 5,693,493, 5,968,493, 6,030,964, 6,133,309, 6,147,244, 6,593,493; H. Kagechiki et al "Retinobenzoic Acids. 2. Structure-Activity Relationship of Chalcone-4-carboxylic Acids and Flavone-4'-carboxylic Acids", *J. Med. Chem.*, 32:834 (1989); H. Kagechika et al "Retinobenzoic Acids. 3. Structure-Activity Relationships of Retinoidal Azobenzene-4-carboxylic Acids and Stilbene-4-carboxylic Acids", *J. Med. Chem.*, 32:1098 (1989); H. Kagechika et al "Retinobenzoic Acids. 4.4 Conformation of Aromatic Amides with Retinoidal Activity. Importance of trans-Amide Structure for the Activity", *J. Med. Chem.* 32:2292 (1989); M. Boehm et al, *J. Med. Chem.* 37:2930 (1994); M Boehm et al, *J. Med. Chem.* 38:3146 (1995); E. Allegretto et al, *Journal of Biol. Chem.*, 270:23906 (1995); R. Bissonnette et al, *Mol. & Cellular Bio.*, 15:5576 (1995); R. Beard et al, *J. Med. Chem.*, 38:2820 (1995); M. I. Dawson et al "Effect of Structural Modifications in the C7-C11 Region of the Retinoid Skeleton on Biological Activity in a Series of Aromatic Retinoids", *J. Med. Chem.*, 32:1504 (1989); and Simoni et al, *Pure Appln. Chem.*, Vol 73, No. 9, pp 1437-1444, 2001. The RAR and RXR retinoid agonists referred to in the abovementioned patent applications, patents and scientific articles may be used in the present invention and have direct application as retinoids in the various therapeutic aspects of this invention described herein. Methods for preparation of retinoids, dosage ranges and compositions/formulations are described in the various patent applications/patents and scientific articles referred to above, and are incorporated herein by reference.

Preferred retinoids include retinoic acid, all-trans retinoic acid, 9-cis-retinoic acid and Eyedrop compositions may be prepared in standard fashion by formulating interferon α, particularly interferon α-2b, in association with one or more ocularly acceptable carriers and excipients. Similarly, the retinoid may be formulated into an eyedrop composition with one or more ocularly acceptable carriers and excipients. Where a combination eyedrop is prepared, both the interferon α and the retinoid are formulated together with one or more ocularly acceptable carriers and excipients.

In accordance with a second aspect of the present invention there is provided an eyedrop formulation of interferon α and retinoid for the combination treatment of ocular lesions, particularly diseases of the surface of the eye, selected from pterygium, pinguecula, ocular dysplasia, ocular neoplastic disorders including malignancy of the limbus and eyelids in humans and animals, neurotrophic keratitis, fibrosis of conjunctival drainage blebs in glaucoma and viral disorders of the eye surface.

Eyedrop formulations include one or more ocularly acceptable carriers and excipients as are known in the art. Eyedrop formulations of interferon α and retinoid may be prepared separately for administration. Alternatively, combined eyedrop formulations of both interferon α and retinoid may be prepared.

Treatment duration according to the various aspects of the present invention are carried out until the disease condition has resolved, or in the alternative is carried out for a period of from one to six months after which the lesion may be surgically removed. Where lesions are neoplastic, and in particular where they are of large size such that they cause discomfort, they are generally surgically removed at the end of treatment. The treatment of the present invention causes extensive necrosis of the lesion thus facilitating surgical removal. Moreover the necrosis of the lesion is believed to prevent lesion recurrence. Treatment according to the present invention is generally in the range from one to six months, although shorter or longer treatment durations may be required depending on the severity of the lesion.

In accordance with a third aspect of the present invention there is provided use of retinoid and interferon α in the manufacture of eyedrop medicaments for the treatment of ocular lesions, particularly diseases of the surface of the eye, selected from pterygium, pinguecula, ocular dysplasia, ocular neoplastic disorders including limbal malignancy including malignancy of the limbus and eyelids in humans and animals, neurotrophic keratitis, fibrosis of conjunctival drainage blebs in glaucoma and viral disorders of the eye surface.

Without wishing to be bound by theory, the inventor believes the combined use of interferon α and retinoid in the eye, which is effective in the treatment of ocular lesions, whereas individual use of such agents is not effective, may be due to a combination of inducement of differentiation of lesion tissue, apoptosis of lesion tissue, inhibition of blood vessels/fibrous tissue associated with lesions and restoration of neural elements.

This invention has particular application to the treatment of ocular lesions in humans and animals. Veterinary applications may be particularly beneficial, for example in treating cattle, horses, other farm animals and domestic animals (including dogs and cats).

The invention will now be described with reference to the following non-limiting examples.

EXAMPLE 1

Mr KB, a 56 year old retired farmer, noted a mass located a the right inferior limbus 12 months prior to presentation.

Figure 1:
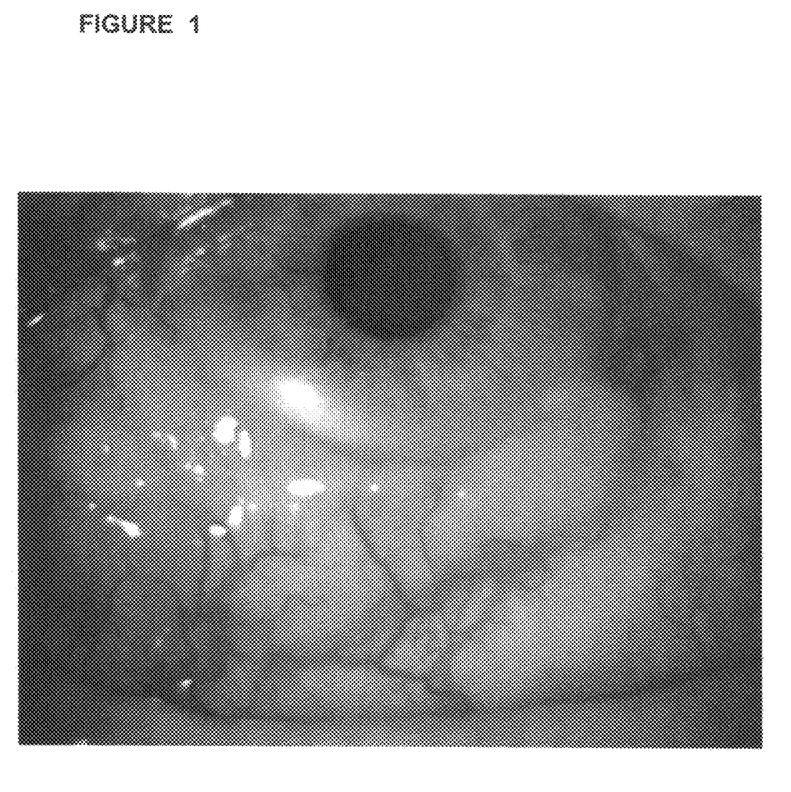
FIG. 1 is a photograph of the eye of Mr KB showing a squamous cell carcinoma clinically extending for 180° at the inferior limbus.

Biopsy revealed a very large squamous cell carcinoma, clinically extending for 180 degrees of the inferior limbus (FIG. 1).

Figure 2:
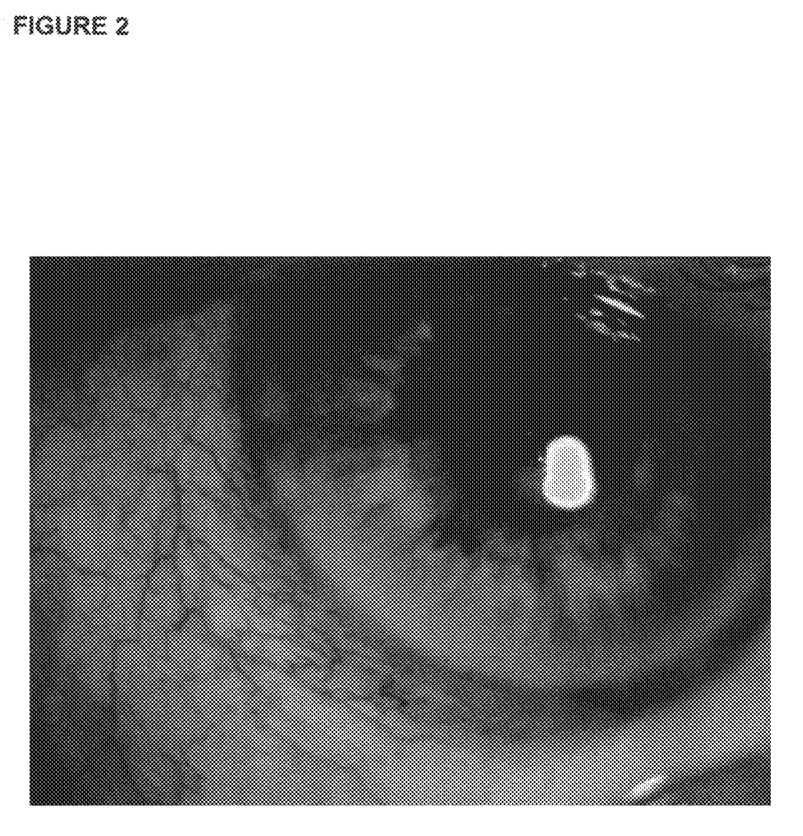
FIG. 2 is a photograph of the eye of Mr KB following treatment according to the invention.

Mr KB was commenced on interferon α-2b 1 million IU qid, retinoic acid 0.01% 2nd daily. He was also treated with intralesional interferon α 3 million IU in 0.5 ml normal saline twice weekly (total 4 injections in 2 weeks) and underwent surgical excision with a limbal-conjunctival graft 6 weeks after treatment commenced. The lesion pathology demonstrated extensive necrosis. There was no evidence of recurrence at 12 month follow up (FIG. 2).

EXAMPLE 2

Figure 3:
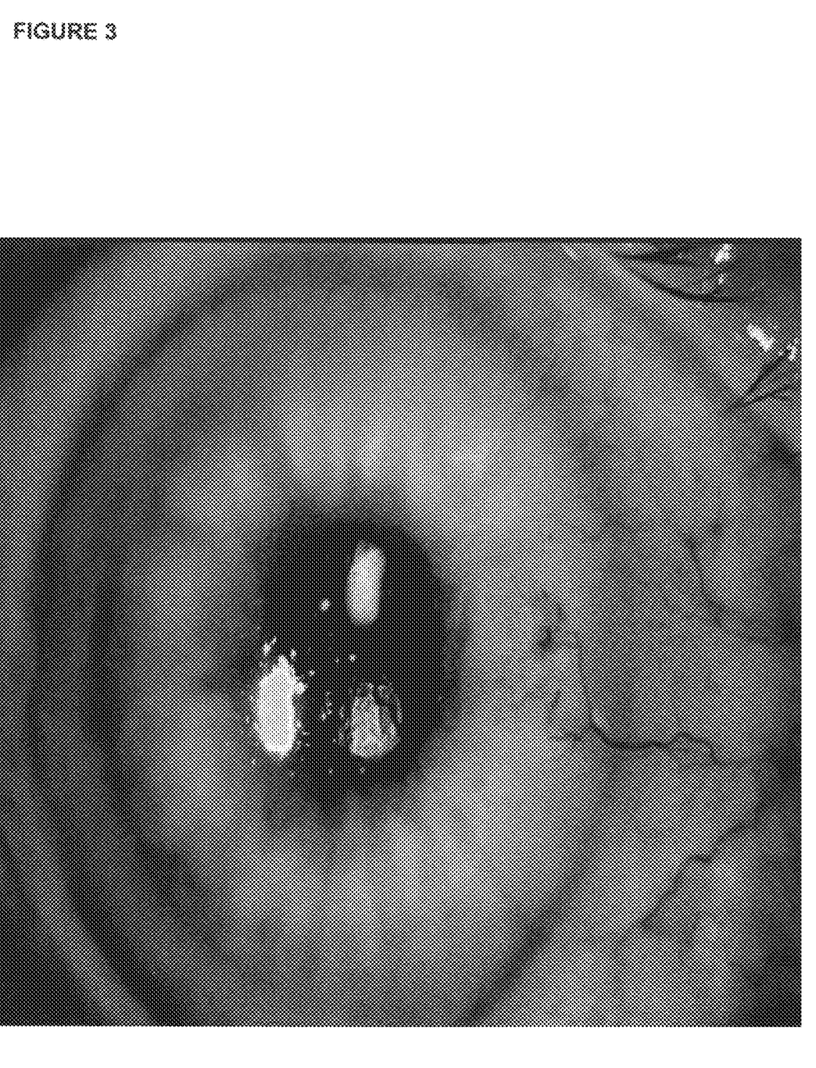
FIG. 3 is a photograph of the eye of Ms BC showing a dense right cataract with a contiguous right nasal pterygium.
Figure 4:
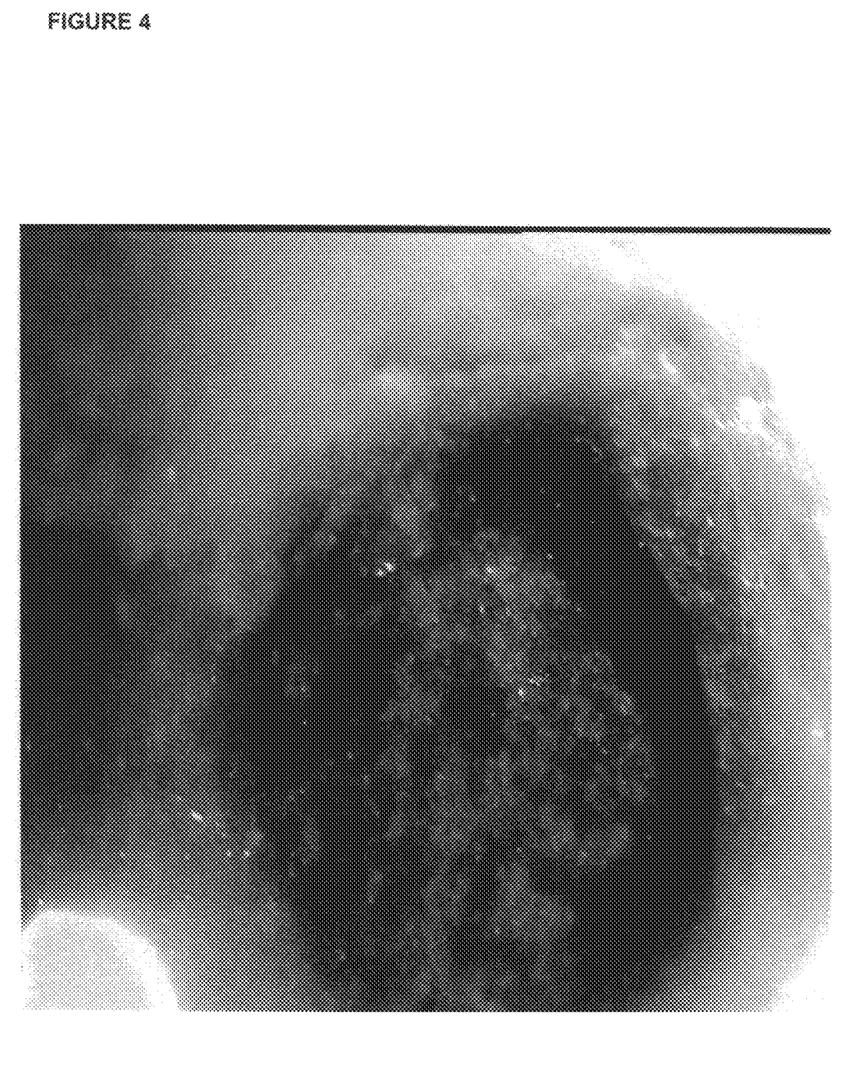
FIG. 4 is a photograph of the eye of Ms BC showing extensive corneal epithelial dysplasia affecting her superior cornea.

Ms BC had a 5 year history of diminishing vision in her right eye, and presented with a dense right cataract and corneal epithelial dysplasia affecting her superior cornea and contiguous with a right nasal pterygium (FIGS. 3 and 4).

Cataract surgery as well as biopsy of a right nasal pterygium with contiguous corneal epithelium was performed. Initial biopsy revealed features consistent with a pterygium. The lesion demonstrated primary acquired melanosis with atypia of the pterygium epithelium.

Figure 5:
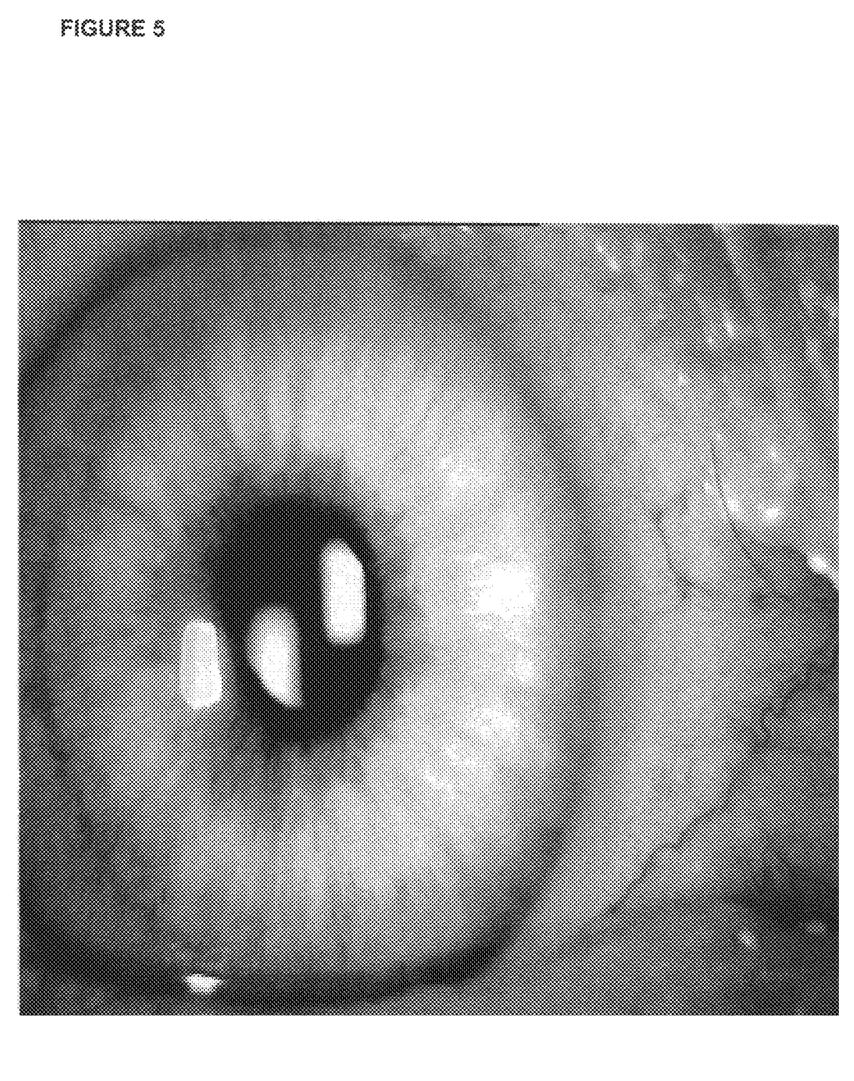
FIG. 5 is a photograph of the right eye of Ms BC following treatment according to the present invention showing resolution of pterygium and epithelial dysplasia.

She was treated with interferon α eyedrops (1 million IU/ml 4 times/day) and retinoic acid eyedrops 0.01% second daily. Three months after combined treatment her vision was stable, corneal epithelial appearance had improved and pterygium has resolved. She was commenced on preservative free serum-based eyedrops and other topical medication ceased. Her vision continued to improved to 6/12 unaided. The pterygium had resolved as had the epithelial dysplasia as shown in FIG. 5.

EXAMPLE 3

Mr KJ presented with a 12 month history of blurred vision in his right eye. The cornea was noted to have reduced sensation and the epithelial surface had broken down on several occasions. Herpetic disease was suspected by a typical dendritic appearance had not been seen. Examination however revealed that the corneal epithelium had a dysplastic appearance. Uncorrected vision in this eye was 6/24 which could not be improved by refraction but pinhole vision was 6/12. He was commenced on retinoic acid eyedrops 0.01% second daily as well as preservative free serum based eyedrops qid. Six months later there had been no improvement and interferon α eyedrops 1 M IU/ml qid were commenced and retinoic acid drops continued as before. After two months of combined treatment there had been a marked improvement in both is corneal appearance with small patch of epithelium of irregular appearance remaining in the super-temporal aspect of his cornea and vision (now 6/12 unaided). He was not able to feel eye drops entering his eye and there was some sensation to testing with a wisp of cotton.

EXAMPLE 4

Figure 6:
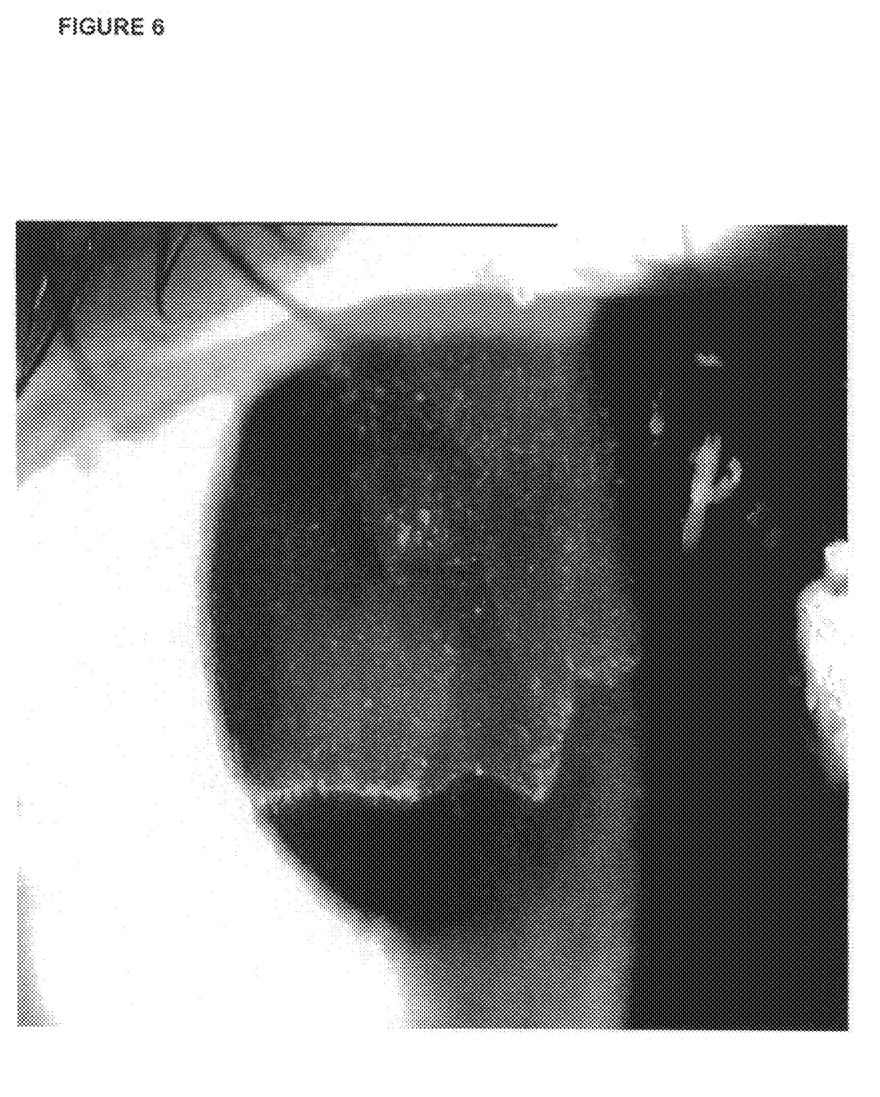
FIG. 6 is a photograph of the eye of Mr GC showing dysplastic epithelium.
Figure 7:
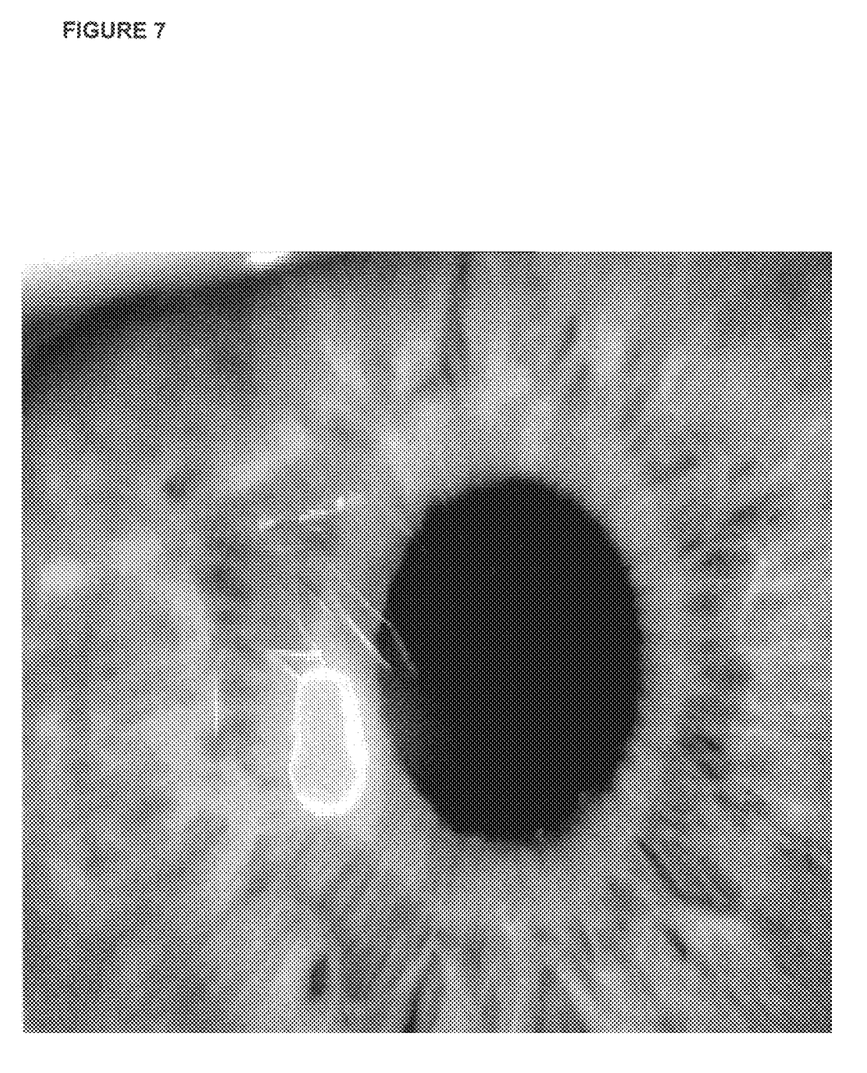
FIG. 7 is a photograph of the eye of Mr GC depicted in FIG. 6 following treatment according to the present invention.

Mr GC initially presented with a central corneal epithelial disturbance and reduced corneal sensation. He was thought to have previously suffered from herpetic keratitis but dendritic lesions had not been seen and his response to topical antiviral agents had been equivocal. His vision was markedly reduced at count fingers (pinhole 6/12). He was also being treated for glaucoma. When Mr GC next presented, some 5½ years later, the superior two thirds of his cornea was covered with dysplastic epithelium and this area was anaesthetic (FIG. 6). He was commenced on retinoic acid 0.01% second daily and interferon α 1 M IU/ml qid. His cornea gradually cleared so that 5 months later his visual acuity had improved to 6/6 unaided and his corneal epithelium appeared normal. There was a marked change in confocal images (FIG. 7).

EXAMPLE 5

UVB-Mediated Induction of Cytokines and Growth Factors in Pterygium Epithelial Cells—Involvement of Cell Surface Receptors and Intracellular Signaling The major focus of this study was to determine whether a MAPK intracellular pathway and mode of signal transmission was involved in the etiology of pterygium. Improved understanding of the immunopathogenesis of pterygia and the relevant molecular pathways that are activated in this common ocular surface disorder will lead to new avenues of treatment that may have relevance to other ocular diseases.

Materials and Methods

UVB-irradiation of Epithelial Cells

All research protocols relating the use of human primary cells were approved by the University of New South Wales Human Ethics Committee and carried out in accordance with the tenets of the World Medical Associations Declaration of Helsinki.

Pterygium-derived epithelial cells (PEC) were seeded at $1 \times 10^6$ cells in 100 mm tissue culture dishes (Corning, N.Y.) or at a density of $1.5 \times 10^5$ cells per well in 6-well plates (Nunc, Denmark) and grown in the presence of 10% FBS/EMEM. Once cells reached semi-confluence, the medium was aspirated, cells washed three times with sterile PBS, and left in serum-free medium for 16 hrs as previously described (Di Girolamo N., et al. *Prog Retin Eye Res.* 2004; 23:195-228), (Di Girolamo N., et al., *Invest Opthalmol Vis Sci.* 2000; 41:671-679), (Di Girolamo N., et al., *Invest Opthalmol Vis Sci.* 2002; 43:3430-3437), (Nolan T, et al., *Am J Pathol.* 2003; 162:567-574), (Di Girolamo., et al., *Invest Ophthalmol Vis Sci.* 2003; 44:4705-4714). In some experiments, cells were pre-incubated with selective inhibitors of ERK1/2, JNK, and p38 MAPKs (Calbiochem, Calif.). These included 10 µM PD98059, 1 µM SB202190, and 1 µM SB203580, respectively. In addition, 1 µM hydrocortisone (Sigma, St Louis, Mich.) was added to some cells as a broad-spectrum negative regulator of cytokine production.

To determine whether surface receptors were involved in transmitting the UVB signal, some cells were pre-incubated for 1 hr with 0.1 µM PD153035 (Calbiochem), an inhibitor of the tyrosine kinase activity of the EGFR or with 0.1 µM AG1295 (Calbiochem) an inhibitor of the tyrosine kinase activity of the PDGFR. While in other experiments, cells were pre-treated with RA (0-0.1 µM; Sigma) or IFN-α (0-15,000 U; PBL Biomedical Laboratories, Piscataway, N.J.). This medium was replaced with PBS and monolayers irradiated with 20 mJ/cm$^2$ of UVB using FL20SE bulbs (Philips, Sydney, Australia) as previously reported (Di Girolamo N., et al. *Prog Retin Eye Res.* 2004; 23:195-228), (Di Girolamo N., et al., *Invest Opthalmol Vis Sci.* 2002; 43:3430-3437), (Nolan T, et al., *Am J Pathol.* 2003; 162:567-574), (Di Girolamo., et al., *Invest Ophthalmol Vis Sci.* 2003; 44:4705-4714). UVB light intensity was monitored and calibrated prior to each experiment with the aid of a radiometer IL1400A (International Light, Newburyport, Mass.). After each exposure, PEC were rinsed once with PBS and placed in fresh serum-free medium with the respective compounds, then incubated for a further 48 hrs. Supernatants were collected, cleared of any cell debris by centrifugation, and stored frozen in small aliquots at −70° C. The compounds used in these experiments were non-toxic at all doses tested.

RNA Extraction and Reverse Transcription Polymerase Chain Reaction

Total RNA was extracted (RNAgents™ Total RNA Extraction Kit, Promega, Sydney, Australia) from mock-irradiated control and UVB-exposed PEC after 24 hrs as previously outlined (Di Girolamo N., et al. *Prog Retin Eye Res.* 2004; 23:195-228), (Di Girolamo N., et al., *Invest Opthalmol Vis Sci.* 2000; 41:671-679), (Di Girolamo N., et al., *Invest Opthalmol Vis Sci.* 2002; 43:3430-3437), (Nolan T, et al., *Am J Pathol.* 2003; 162:567-574), (Di Girolamo., et al., *Invest Ophthalmol Vis Sci.* 2003; 44:4705-4714). Reverse transcription was performed according to the manufacturer's instructions (Preamplification system for first strand cDNA synthesis kit, Gibco BRL, Gaithersburg, Md.) as previously described, (Di Girolamo N., et al., *Invest Opthalmol Vis Sci.* 2000; 41:671-679), (Di Girolamo N. et al., *Invest Ophthalmol Vis Sci.* 2001; 42:1963-1968.), (Di Girolamo N., et al., *Invest Opthalmol Vis Sci.* 2002; 43:3430-3437), (Nolan T, et al., *Am J Pathol.* 2003; 162:567-574), (Di Girolamo., et al., *Invest Ophthalmol Vis Sci.* 2003; 44:4705-4714), (Di Girolamo N., et al. *Am J Pathol.* 2005). Aliquots (1 µl) of cDNA were amplified by PCR using 100 nM each of the forward and reverse gene specific primers for IL-6[19], IL-8[19], VEGF (reverse 5'-TCG ATC GTT CTG TAT CAG TCT-3'; forward 5'-CCA TGA ACT TTC TGC TGT CTT-3') and GAPDH, (Di Girolamo N., et al., *Invest Opthalmol Vis Sci.* 2002; 43:3430-3437), (Nolan T, et al., *Am J Pathol.* 2003; 162:567-574), (Di Girolamo., et al., *Invest Ophthalmol Vis Sci.* 2003; 44:4705-4714), (Di Girolamo N., et al. *Am J Pathol.* 2005). Initially, a 2 min hot start at 95° C. was performed to denature the double stranded cDNA, followed by 26-32 cycles of PCR (each cycle: 95° C., 30 sec; 55° C., 30 sec; 72° C., 30 sec), and the reactions terminated with a 2 min extension at 72° C. Cycle number was determined so that the products formed fell within the linear portion of the amplification curve. PCR products were visualized on either 1.2 or 2% agarose gels that contained ethidium bromide. Semi-quantitative assessment was performed after normalization to GAPDH with the Gel Doc 2000™ (Bio Rad, Sydney, Australia) and the Quantity One™ program (Bio Rad).

Enzyme Immunoassays

Human IL-6, IL-8, and VEGF (Quantikine™; R&D Systems, Minneapoli, Minn.) were quantified using sandwich immunoassays. Cytokines in supernatants from control (mock irradiated), or UVB-exposed PEC were captured on antibody-coated 96-well plates, and detection performed precisely as directed by the manufacturer. The optical density of the reaction product was read at the appropriate wavelength using a microplate reader (Spectramax™ Plus, Molecular Devices, Sunnyvale, Calif.).

Multi-Cytokine Analysis

Multiplex cytokine array analysis was performed using the protein multi-array system (Bio-Plex™, BioRad). The 8-plex anti-human assay kit (IL-2, -4, -6, -8, -10, -12, -13, TNF-α) was used according to the manufacturer's recommendations. Cytokine concentration in undiluted supernatants (100 µl) was quantified against standards provided in the kit.

Statistical Analysis

Cytokine levels in the culture supernatants were expressed as mean±standard deviation. Difference in cytokine level between control and UV treated cells was assessed by one-way analysis of variance, followed by the Newman-Keuls test for multiple comparisons of treatment groups with the control group. A commercial software package (Prism; GraphPad Software, San Diego, Calif.) was used for analysis.

Results

UVB Radiation Induces Cytokine and Growth Factor mRNA Expression

PEC were exposed to a single dose (20 mJ/cm$^2$) of UVB radiation to determine whether cytokine and growth factor mRNA could be modulated. These results indicate that this level of UV induced the expression of two potent pro-inflammatory mediators, namely IL-8 and IL-6 by 5.2- and 1.7-fold, respectively.

In the current investigation, it was noted that VEGF mRNA was increased by 1.5-fold following UVB exposure. This now adds another effector molecule to the growing list of UV-sensitive mitogens that may be implicated in the development of this disease.

Induction of IL-6, IL-8, and VEGF is Mediated by MAPK Pathways

To determine whether cytokine and growth factor induction following UVB exposure was mediated by a MAPK pathway, PEC were irradiated and/or treated with specific intracellular pathway inhibitors. Initially, it was noted that up-regulated IL-8, IL-6, and VEGF protein production occurred following UVB, a result that paralleled the increased gene transcription. Interestingly, the addition of specific MAPK inhibitors (SB202190, SB203580, PD98059) significantly abrogated IL-8, IL-6, and VEGF production post-radiation. These inhibitors inhibited IL-8 and IL-6, while VEGF production was only partially, but significantly reduced. Hydrocortisone suppressed the production of all three proteins to near control levels, while the diluent control (DMSO) had no significantly effect on cytokine expression.

Cell-Surface Receptors are Signal Transmitters

It was postulated that cell-surface receptors might function as transmitters of the UVB signal. The present study demonstrated that EGFR, but not PDGFR, was responsible for relaying the UVB signal that resulted in increased IL-8 production. The addition of PD153035 significantly reduced IL-8 levels from 166.6±22.5 pg/ml to 74.4±23.6 pg/ml ($p<0.01$) whereas AG1295 had a negligible effect (174.4±60.3 µg/ml). In contrast to IL-8, the UVB-mediated induction of IL-6 predominantly involved signal transmission through the PDGFR as the PDGFR inhibitor (AG1295) significantly reduced IL-6 levels from 356.2±32.1 to 217±42 pg/ml ($p<0.01$). PD153035 (109.1±1.5 pg/ml) and AG1295 (132.7±8.0 pg/ml) moderately suppressed ($p<0.01$) VEGF production compared to UVB alone (166.5±11.0 pg/ml), thus implicating both receptors in signal transmission.

Retinoic Acid and Interferon-α Inhibit IL6 and -8 Production

Diseased ocular surface epithelial cells were exposed to a single dose of UVB then treated with several concentrations of RA and IFN-α. Both drugs dose-dependently inhibited IL-8 and IL-6 protein production but had no significant inhibitory effect on the UVB-mediated induction of VEGF.

The invention claimed is:

1. A method for the non-surgical treatment of an ocular dysplastic or neoplastic lesion, comprising administering to the surface of the eye of a subject in need of such treatment, a therapeutically effective amount of interferon α and a retinoid, wherein the interferon α and the retinoid are administered concurrently, or are administered sequentially with a time interval between interferon α administration and retinoid administration of up to 36 hours.

2. The method according to claim 1, wherein the interferon α and the retinoid are administered sequentially with time interval between interferon α administration and retinoid administration of from 24 to 36 hours.

3. The method according to claim 1, wherein the interferon α and retinoid are instilled onto the surface of the eye by using an eyedrop composition.

4. The method according to claim 1, wherein the interferon α is administered by injection into said lesion.

5. The method according to claim 1, wherein the interferon α is α2b.

6. The method according to claim 1, wherein the retinoid is all-trans retinoic acid.

7. The method according to claim 1, wherein the retinoid is retinoic acid.

8. The method according to claim 1, wherein the retinoid is 9-cis retinoic acid or a compound of the formula:

9. The method according to claim 1, wherein said interferon α is administered in an amount of from about 0.2 million to about 5 million international units.

10. The method according to claim 9, wherein said interferon α is administered in an amount of from about 1 million to about 3 million international units.

11. The method according to claim 1, wherein said retinoid is administered in an amount of from about 0.01 to about 0.15% w/w.

12. The method according to claim 11, wherein said retinoid is administered in an amount of from about 0.05 to about 0.1% w/w.

13. The method of claim 1, wherein the interferon α is administered at least once daily, and the retinoid is administered once every two or more days.

14. The method of claim 13, wherein the interferon α is administered at least 4 times daily.

15. The method of claim 1, wherein said ocular neoplastic lesion is a malignancy of the limbus or eyelids.

16. A method for the non-surgical treatment of an ocular lesion resulting from proliferation of ocular tissue, comprising administering to the surface of the eye of a subject in need of such treatment, a therapeutically effective amount of interferon α and a retinoid for a period of 1-6 months, wherein the interferon α and the reintoid are administered concurrently, or are administered sequentially with a time interval between interferon α administration and retinoid administration of up to 36 hours.

17. The method according to claim 16, wherein the interferon α and the retinoid are administered sequentially with a time interval between interferon α administration and retinoid administration of from 24 to 36 hours.

18. The method according to claim 16, wherein the interferon α and retinoid are instilled onto the surface of the eye by using an eyedrop composition.

19. The method according to claim 16, wherein the interferon α is administered by injection into said lesion.

20. The method according to claim 16, wherein the interferon α is α2b.

21. The method according to claim 16, wherein the retinoid is all-trans retinoic acid.

22. The method according to claim 16, wherein the retinoid is retinoic acid.

23. The method according to claim 16, wherein the retinoid is 9-cis retinoic acid or a compound of the formula:

24. The method according to claim 16, wherein said interferon α is administered in an amount of from about 0.2 million to about 5 million international units.

25. The method according to claim 24, wherein said interferon α is administered in an amount of from about 1 million to about 3 million international units.

26. The method according to claim 16, wherein said retinoid is administered in an amount of from about 0.01 to about 0.15% w/w.

27. The method according to claim 26, wherein said retinoid is administered in an amount of from about 0.05 to about 0.1% w/w.

28. The method of claim 16, wherein the interferon α is administered at least once daily, and the retinoid is administered once every two or more days.

29. The method of claim 28, wherein the interferon α is administered at least 4 times daily.

30. The method of claim 16, wherein said ocular lesion is the result of a disease of the surface of the eye selected from the group consisting of pterygium, pinguecula, ocular dysplasia, an ocular neoplastic disorder, neurotrophic keratitis, fibrosis of conjunctival drainage blebs in glaucoma and a viral disorder of the eye surface.

31. The method of claim 30, wherein said ocular neoplastic disorder is a malignancy of the limbus or eyelids.

* * * * *